United States Patent [19]
El Maoued

[11] Patent Number: 5,769,818
[45] Date of Patent: Jun. 23, 1998

[54] BAG CATHETER PROVIDING COMPLETE BLADDER DRAINAGE

[75] Inventor: Adel A. El Maoued, 1312 Gnakomis Dr., NE, Albuquerque, N. Mex. 87112

[73] Assignees: Adel A. El Maoued, Albuquerque, N. Mex.; Kalil M. Jiraki, Detroit, Mich.

[21] Appl. No.: 819,116

[22] Filed: Mar. 17, 1997

[51] Int. Cl.$^6$ .................................................. A61M 25/00
[52] U.S. Cl. ............................................. 604/96; 604/101
[58] Field of Search ............................. 604/96, 101, 327, 604/328; 606/192, 194

[56] References Cited

U.S. PATENT DOCUMENTS

| | | | |
|---|---|---|---|
| 3,409,016 | 11/1968 | Foley . | |
| 4,575,371 | 3/1986 | Nordqvist et al. | 604/96 |
| 5,616,126 | 4/1997 | Malekmehr et al. | 604/96 |
| 5,645,528 | 7/1997 | Thome | 604/96 |

*Primary Examiner*—Corrine M. McDermott
*Attorney, Agent, or Firm*—Peter D. Keefe

[57] ABSTRACT

A bag catheter enabling complete drainage of the bladder characterized by a flexible shaft of rubber, silicone treated rubber, or, preferably, silicone, wherein a distal end is rounded for insertion into the urethra and the opposite, proximate end is structured for interfacing with a urine collector. The shaft includes a drainage tube and an inflation channel, the inflation channel preferably being interfaced with a conventional distension tube with self-sealing membrane. The drainage tube opens at the proximate end of the shaft and has a first drainage portal, preferably also including a conventional second drainage portal as well, at the distal end portion of the shaft. At least one balloon is located at the distal end portion of the shaft, wherein the first drainage portal is located at the site of the at least one balloon. In this regard, the at least one balloon inflates outwardly in relation to the shaft and outwardly around the first drainage portal when pressurized fluid is introduced into the inflation channel. Because the at least one balloon has inflated outwardly around the first drainage portal, urine collecting immediately adjacent the urethro-vesical junction passes thereinto and is discharged from the bladder via the drainage tube.

18 Claims, 3 Drawing Sheets

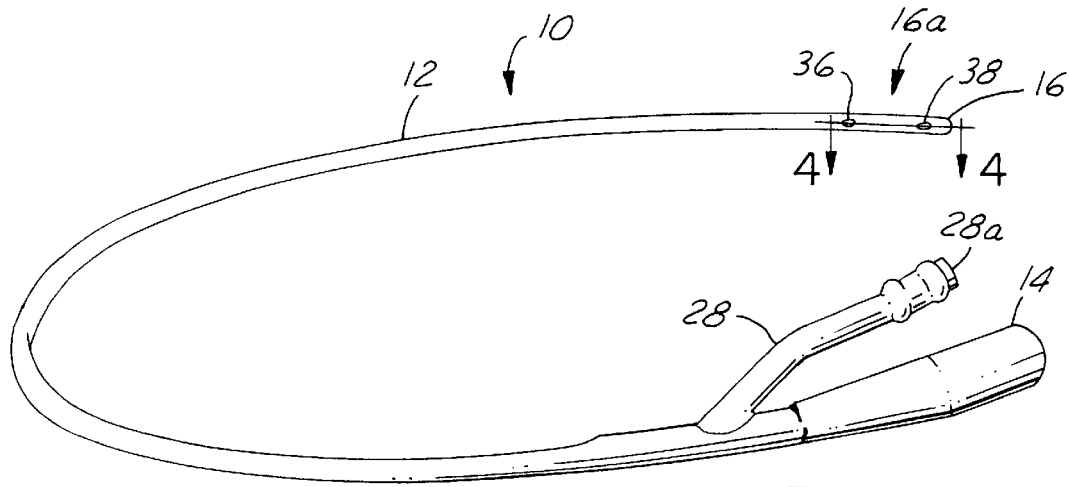
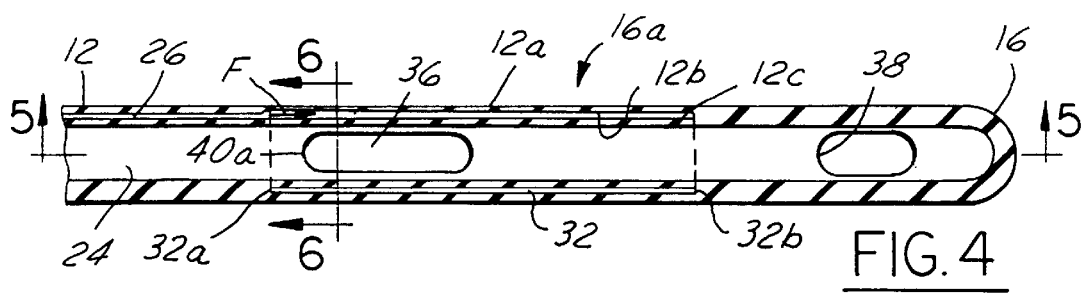
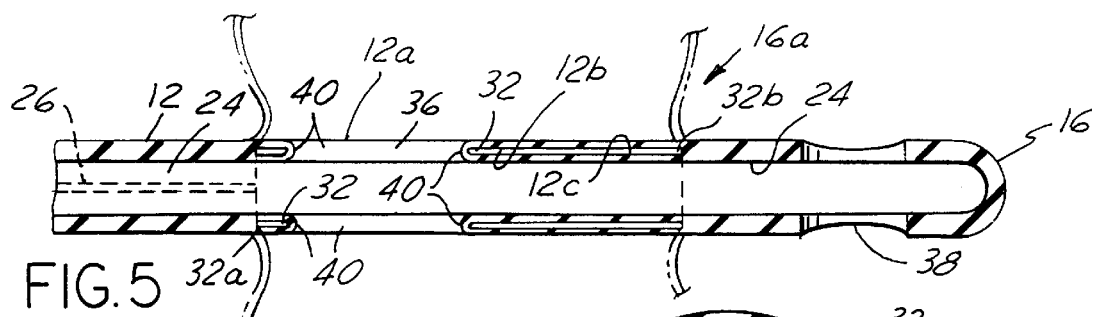
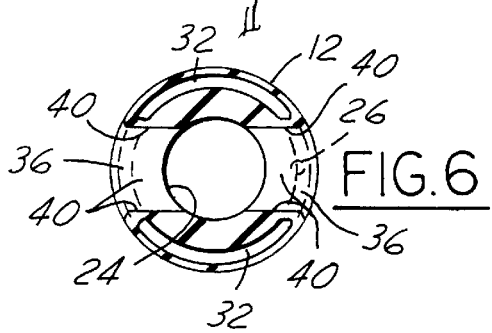
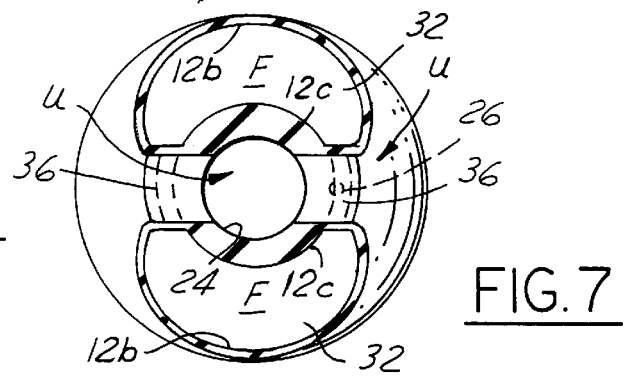

BAG CATHETER PROVIDING COMPLETE BLADDER DRAINAGE

BACKGROUND OF THE INVENTION

1. Field of the Invention

The present invention relates to bag catheters used for drainage of urine from the bladder, and more particularly to a bag catheter having an improved drainage portal provision for substantially completely draining the bladder.

2. Description of the Prior Art

Bag catheters are routinely used by physicians for draining urine from the bladder of their patients. The standard bag catheter includes an elongated flexible shaft which is commonly composed of surgical rubber, silicone treated rubber, or silicone. The shaft has two components, a drainage tube and an inflation channel. The drainage tube generally runs the length of the shaft, wherein the shaft has a proximate end and an opposite distal end. The distal end is rounded for being inserted into the urethra and thereupon into the bladder and is provided adjacent the distal end with a drainage portal for passing urine from the bladder into the drainage tube. The proximate end remains outside the patient's body and terminates at a urine collection site. In order that the distal end portion of the shaft remains situated in the bladder such that the drainage portal can receive urine therefrom, an inflatable balloon is situated near the drainage port at a location relatively more remote with respect to the distal end. The inflated balloon may also serve to seal the opening of the urethra at the bladder (the urethro-vesical junction) against urine leaking out of the bladder exterior with respect to the shaft.

The balloon is structured to inflate exteriorly with respect to the shaft, whereby when inflated the balloon cannot exit the bladder. Accordingly, the distal end portion of the shaft, along with the drainage portal, is prevented from exiting the bladder, as well. In order for the balloon to be selectively inflated (it must not be inflated until it has, itself, passed entirely into the bladder) the inflation channel is in fluid communication with the balloon, whereby fluid under pressure is introduced to inflate the balloon via the inflation channel Typically, the inflation channel includes a distension tube which exits the shaft in advance of the proximate end thereof. The terminous of the distension tube has a self-sealing membrane through which a hypodermic syringe (or other device) is inserted to introduce (or remove) pressurized fluid with respect to the balloon. An example of an interesting bag catheter structure is described in U.S. Pat. No. 3,409,016 to Foley, dated Nov. 5, 1968. It is notable in regard to this patentee, that frequently bag catheters are referred to as Foley catheters.

Problematically, conventional bag catheters do not ensure full drainage of the bladder. This is because the drainage portal is located between the balloon and the distal end of the shaft thereby resulting in the drainage portal being distantly spaced away from the urethro-vesical junction (as well as the balloon which occupies the immediate area). Accordingly, any urine collecting in the bladder between the urethro-vesical junction and the drainage portal will stay in the bladder and cannot be drained. Lack of complete drainage can result in or exacerbate bladder infection or other medical conditions, such as low lying bladder fistulas as for example a vesico-vaginal fistula at the trigone. Therefore, what remains needed in the art is a bag catheter which is structured so as to enable complete drainage of the bladder.

SUMMARY OF THE INVENTION

The present invention is a bag catheter which is structured so as to enable complete drainage of the bladder.

The bag catheter according to the present invention is characterized by a flexible shaft of rubber, silicone treated rubber, or, preferably, silicone, wherein a distal end is rounded for insertion into the urethra and the opposite, proximate end is structured for interfacing with a urine collector. The shaft includes a drainage tube and an inflation channel, the inflation channel preferably being interfaced with a conventional distension tube with self-sealing membrane. The drainage tube opens at the proximate end of the shaft and has a first drainage portal, preferably also including a conventional second drainage portal as well, at the distal end portion of the shaft. At least one balloon is located at the distal end portion of the shaft, wherein the first drainage portal is located at the site of the at least one balloon. In this regard, the at least one balloon inflates outwardly in relation to the shaft and outwardly around (that is, away from) the first drainage portal when pressurized fluid is introduced into the inflation channel, as per the design of the balloon or balloons.

In operation, the distal end of the shaft is inserted into the patient's urethra so that the distal end portion thereof enters the bladder. Thereafter, pressurized fluid is introduced into the inflation channel, thereby inflating the at least one balloon. The at least one balloon inflates outwardly in relation to the shaft and outwardly around or adjacent the first drainage portal, and thereupon is too large in relation to the size of the urethro-vesical junction for the distal end portion to be slidable outwardly from the bladder. Because the at least one balloon has inflated outwardly around the first drainage portal without occluding it, urine collecting immediately adjacent the urethro-vesical junction passes thereinto and is discharged from the bladder via the drainage tube.

Accordingly, it is an object of the present invention to provide a bag catheter which enables complete urine drainage from the bladder of a patient immediately adjacent the urethro-vesical junction.

It is a further object of the present invention to provide a bag catheter, the at least one balloon of which inflating in relation to a drainage portal situated thereat, whereby urine is drainable from a patient's bladder immediately adjacent (above) the urethro-vesical junction.

These, and additional objects, advantages, features and benefits of the present invention will become apparent from the following specification.

BRIEF DESCRIPTION OF THE DRAWINGS

FIG. 3 is a perspective view of the bag catheter according to the present invention, shown in the uninflated state.

FIG. 4 is a partly sectional view of the bag catheter, seen along line 4—4 in FIG. 3.

FIG. 5 is a partly sectional view of the bag catheter, seen along line 5—5 in FIG. 4.

FIG. 6 is a partly sectional view of the bag catheter, seen along line 6—6 in FIG. 4, wherein the balloon is in its uninflated state.

FIG. 7 is a partly sectional view of the bag catheter, seen as in FIG. 6, wherein the balloon is in its inflated state.

DETAILED DESCRIPTION OF THE PREFERRED EMBODIMENT

Figure 1:
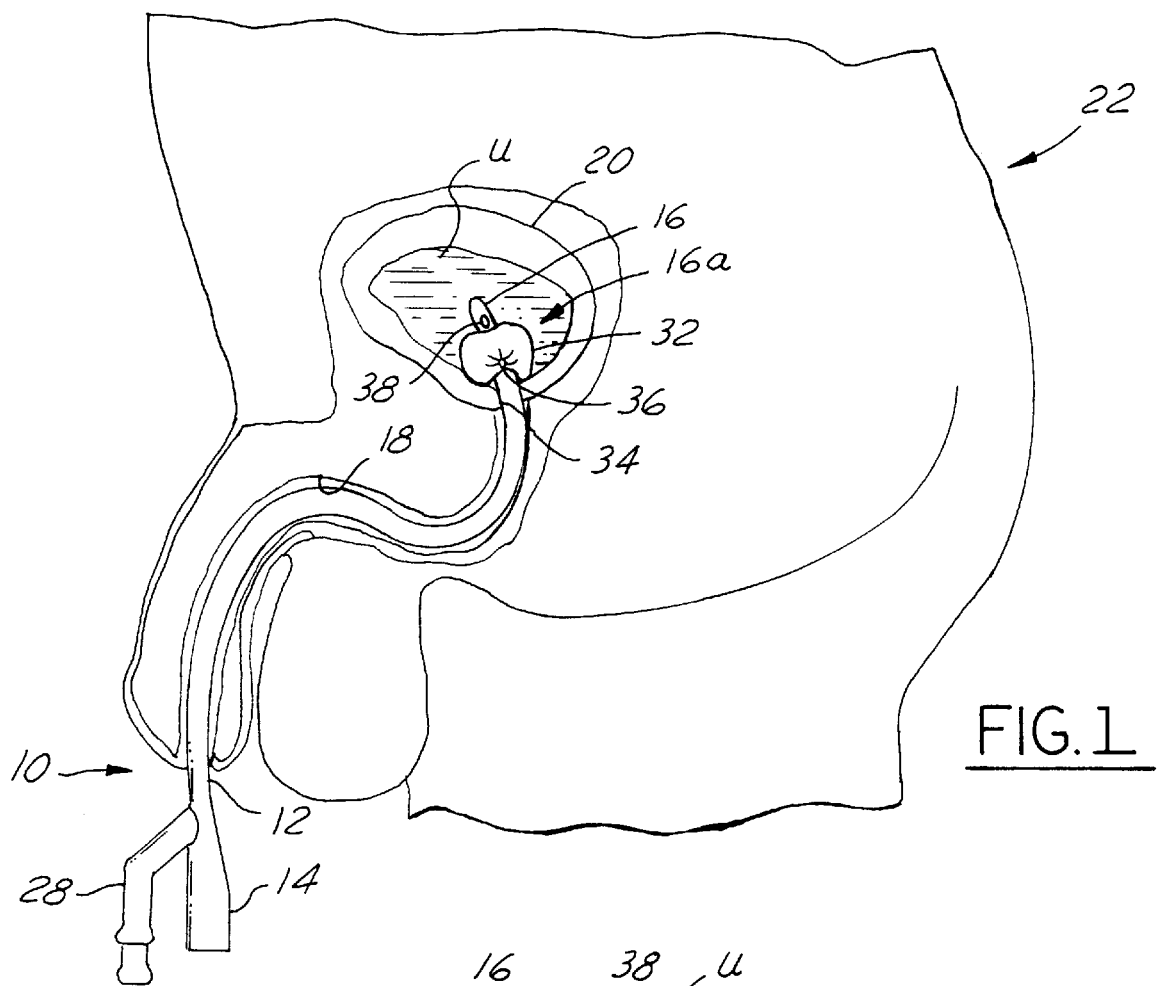
FIG. 1 is a partly sectional side view, showing a single balloon bag catheter according to the present invention in operation with respect to a patient.
Figure 2:
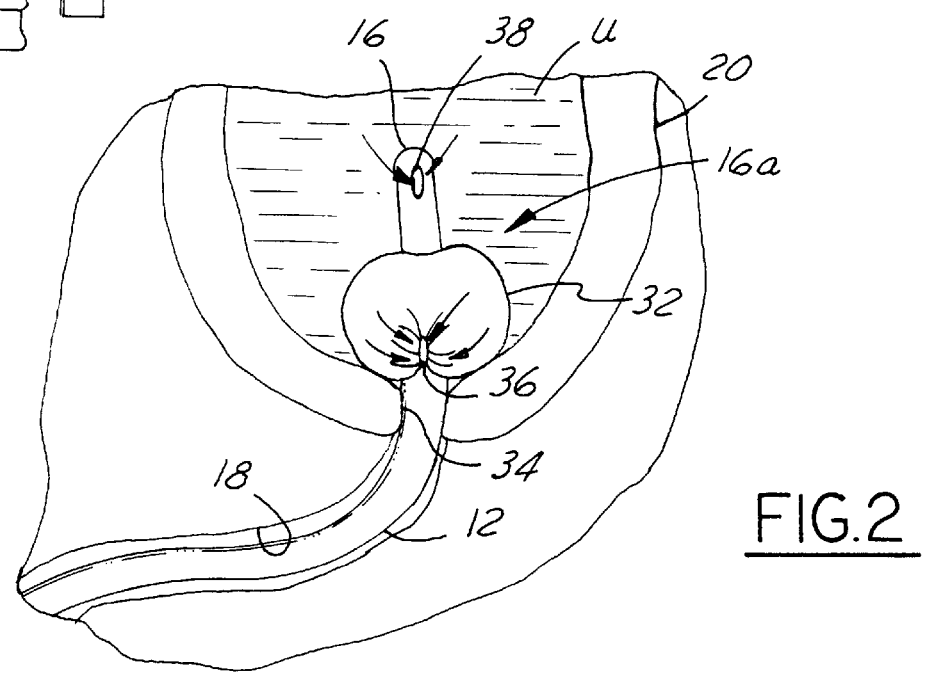
FIG. 2 is a detail side view of the bag catheter and the bladder of the patient as shown in FIG. 1.
Figure 8:
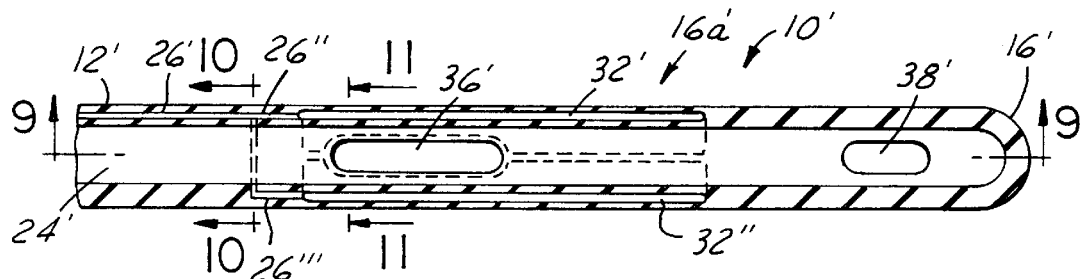
FIG. 8 is a partly sectional view of a plurality balloon bag catheter, showing the distal end portion thereof.
Figure 9:
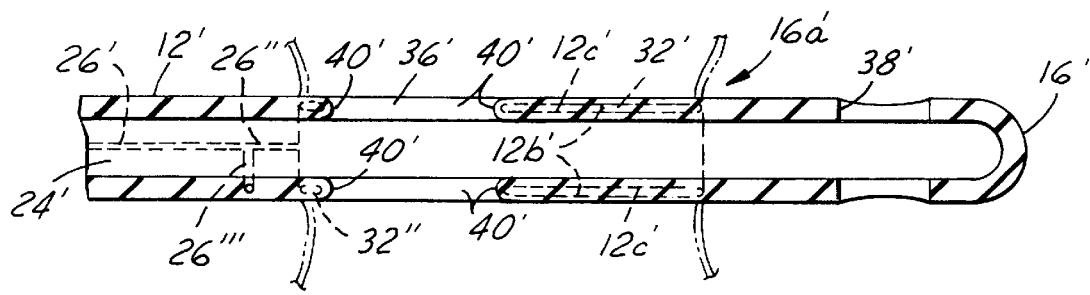
FIG. 9 is a partly sectional view of the bag catheter, seen along line 9—9 in FIG. 8.
Figure 10:
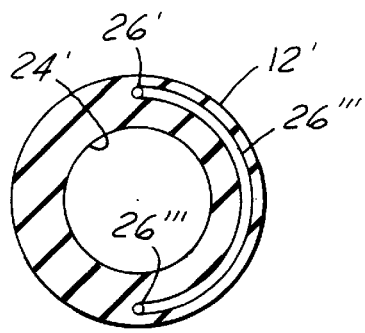
FIG. 10 is a partly sectional view of the bag catheter, seen along line 10—10 in FIG. 8.

Referring now to the Drawing, FIGS. 1 and 2 generally depict environmental views of operation of the bag catheter according to the present invention; FIGS. 3 through 7 depict structural aspects of a bag catheter according to the present invention having a single balloon; and FIGS. 8 through 12 depict structural aspects of a bag catheter according to the present invention having a plurality of balloons.

Referring firstly to the bag catheter according to the present invention having a single balloon, FIG. 3 depicts the bag catheter 10 according to the present invention. The bag catheter 10 includes a flexible shaft 12 having a proximate end 14 and an opposite distal end 16, wherein the proximate end is open and/or otherwise adapted in a conventional manner to interface with a urine collector, and wherein the distal end is rounded for facilitating sliding insertion through the urethra 18 into the bladder 20 of a patient 22 (see FIG. 1).

The shaft 12 is composed of conventional material, such as for example rubber, silicone treated rubber, or, preferably, silicone. The shaft 12 is composed of a drainage tube 24 and an inflation channel 26 (see FIGS. 4 through 7). A distension tube 28 sealingly interfaces with the shaft 12, and provides a conventional self-sealing membrane structure 28a (or other structure) for a medical care-giver to introduce pressurized fluid into the inflation channel 26. In this regard, the distension tube 28 is in fluidic communication with the inflation channel 26, but not the drainage tube 24. Indeed, the inflation channel 26 and the drainage tube 24 are mutually exclusively fluidically sealed so that no fluid exchange therebetween is possible.

The purpose of the drainage tube 24 is to provide drainage of urine U from a patient's bladder 20 into a urine collector (not shown) external to the body of the patient 22. The purpose of the inflation channel 26 (and its associated distension tube 28) is to provide selective inflation of a balloon 32 located at the distal end portion 16a of the shaft 12, whereby when the balloon is inflated the end portion of the shaft is prevented from slidingly passing through the urethro-vesical junction 34 of the bladder (see FIGS. 1 and 2).

The structures associated with the balloon 32 of the bag catheter 10 is different from that associated with a conventional balloon of a conventional bag catheter. In this regard, a first drainage portal 36 is provided in the shaft 12 which is situated at the situs of the balloon 32. The first drainage portal 36 passes directly through-and-through the shaft 12, wherein the shaft is apertured thereby so as to provide fluidic communication of the drainage tube 24 with the environment external to the shaft (see FIG. 5).

As shown best by FIG. 4, the first drainage portal 36 is preferred to be elongated about 15 mm. along the axis of the shaft 12. Further, it is preferred to locate the proximate wall 40a of the first drainage portal 36 about 1 to 2 mm. from the proximate side 32a of the balloon 32 in a direction toward the distal end 16 (see FIG. 4). This configuration and location provides a facilitated flowage of urine from the bladder 20 in the immediate vicinity of the urethro-vesical junction 34, as will be detailed hereinbelow.

The balloon 32 is situated in the sidewall 12a of the shaft 12, having a preferred elongation along the axis of the shaft of about 35 mm. As shown by FIGS. 6 and 7, the balloon 32 is, itself, sealed in relation to the walls 40 of the first drainage portal 36. The balloon 32 is defined by an outer sidewall 12b, an inner sidewall 12c, the internal sides of the first drainage portal and the proximate and distal ends 32a, 32i b of the balloon, wherein the outer and inner sidewalls are mutually sealed. The balloon 32 may be directly formed integrally within a simply connected sidewall 12a of the shaft 12, formed by the outer sidewall 12b being laid over the inner sidewall 12c during a forming step, or formed by any suitable method known in the art. When the balloon 32 is inflated, pressurized fluid F has been introduced thereinto. As shown at FIGS. 1, 2 and 7, even though the balloon 32 is inflated, the first drainage portal 36 is not occluded by the balloon, and urine U is able to pass therethrough from the bladder 20 into the drainage tube 24.

Preferably, a conventional second drainage portal 38 is provided in the shaft 12 near the distal end 16. In this regard, the second drainage portal 38 communicates with the drainage tube 24, so that urine U will drain from the bladder 20 in a conventional manner into the drainage tube 24 as an augmentation of the hereinabove recounted urine drainage through the first drainage portal 36.

In operation, a medical care-giver inserts the shaft 12, distal end 16 first, into the urethra 18 of a patient 22 so that the distal end portion 16a passes through the urethro-vesical junction 34 and enters into the bladder 20. The medical care-giver then interfaces the proximate end of the shaft with respect to a urine collector so that urine exiting from the drainage tube 24 is collected external to the patient. The medical care-giver next interfaces a conventional pressurized fluid generating device, such as for example a syringe, into the self-sealed end 28a of the distension tube 28, and then introduces pressurized fluid into the distension tube. The pressurized fluid flows into the inflation channel 26 and thereupon into the balloon 32. The balloon inflates outwardly in relation to the shaft 12 and outwardly around the first drainage portal 36, whereby the first drainage portal remains unobstructed by the inflating balloon. When inflated, the balloon 32 abuts the urethro-vesical junction 34 and is too large to slidably pass therethrough. Consequently, the distal end portion 16a of the shaft 12 is trapped in the bladder 20.

Now, the first drainage portal receives urine collecting in the bladder in general, including, uniquely, any urine U collecting in the vicinity of the urethro-vesical junction 34. Where a conventional second drainage portal 38 is present, this will also drain urine U to the extent it can, in that the second drainage portal is located in spaced relation with respect to the urethro-vesical junction.

As mentioned hereinabove, it is preferred to locate the proximate wall 40a of the first drainage portal 36 about 1 to 2 mm. from the proximate side 32a of the balloon 32 in a direction toward the distal end of the shaft. In this regard, the proximate side of the balloon may in part enter into the urethro-vesical junction. As a result, by placing the balloon drainage portal from about 1 to 2 mm. therefrom, in is likely that the first drainage portal will not be at all occluded by the urethro-vesical junction. However, the placement of the first drainage portal may be other than that preferred.

As indicated hereinabove, while a single balloon is most preferred, a plurality of balloons may be used. Referring now to a bag catheter according to the present invention having a plurality of balloons, FIGS. 8 through 12 show a two balloon configuration bag catheter 10', wherein primes on numerals designate components having like structure and function to that of the above detailed single balloon bag catheter 10. Accordingly, for the sake of brevity, further detailed discussion of the bag catheter 10' shall be hereinbelow confined to the differences thereof with respect to the bag catheter 10. It should be noted that while two balloons 32', 32" are depicted at FIGS. 8 through 12, it is to be understood that the plurality of balloons may be a number thereof greater than two.

The bag catheter 10' has a shaft 12' having a drainage tube 24' and an inflation channel 26', and further has other features as discussed hereinabove with respect to the bag catheter 10, however, now there are two balloons, a first balloon 32' and a second balloon 32". The first and second balloons 32', 32" are each located, respectively, at either side of the first drainage portal opening 36'. The inflation channel 26' now has a first branch channel 26" which fluidically communicates with the first balloon 32', and a second branch channel 26''' which fluidically communicates with the second balloon 32".

Figure 12:
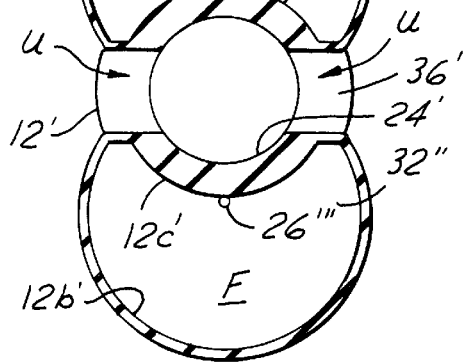
FIG. 12 is a partly sectional view of the bag catheter, seen as in FIG. 11, wherein the balloons are in their inflated state.
Figure 11:
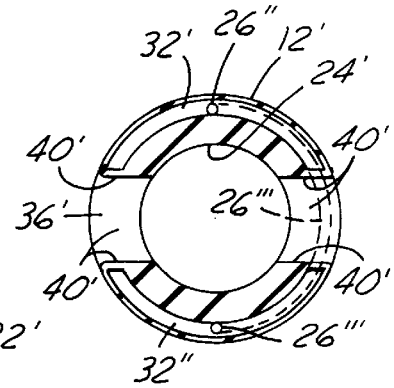
FIG. 11 is a partly sectional view of the bag catheter, seen along line 11—11 in FIG. 8, wherein the balloons are in their uninflated state.

The plurality balloon bag catheter 10' operates as discussed with respect to the single balloon bag catheter 10. When the first and second balloons 32', 32" are inflated as shown in FIG. 12, via the inflation channel 26', urine U freely enters the first drainage portal 36' while the first and second balloons abut the urethro-vesical junction in the general manner depicted in FIGS. 1 and 2 with respect to the single balloon bag catheter 10.

To those skilled in the art to which this invention appertains, the above described preferred embodiment may be subject to change or modification. Such change or modification can be carried out without departing from the scope of the invention, which is intended to be limited only by the scope of the appended claims.

What is claimed is:

1. A bag catheter comprising:
    an elongated flexible shaft having a proximate end and an opposite distal end, a distal end portion of said shaft including said distal end, said flexible shaft comprising:
        a first drainage portal formed in said shaft at a predetermined situs of said distal end portion;
        a drainage tube formed in said shaft, said drainage tube fluidically communicating with said first drainage portal;
        at least one balloon having a proximal end and a distal end, said balloon being attached to said shaft between said proximal and distal ends of said balloon, wherein said proximal and distal ends of said balloon are located on either side of said first drainage portal; and
        channel means fluidically communicating with said at least one balloon for inflating said at least one balloon when a pressurized fluid is introduced into said channel means;
        wherein said at least one balloon inflates outwardly in relation to said shaft and outwardly in relation to said first drainage portal without occluding said first drainage portal.

2. The bag catheter of claim 1, wherein said channel means comprises:
    seal means for fluidically sealing said at least one balloon with respect to said first drainage portal; and
    fluid channel means for selectively introducing the pressurized fluid to said at least one balloon;
    wherein said fluid channel means and said drainage tube are respectively sealed so that said fluid channel means and said drainage tube are fluidically independent of each other.

3. The bag catheter of claim 2, wherein said fluid channel means comprises:
    an inflation channel; and
    fluid entry means for providing a site of introduction of the pressurized fluid into said inflation channel.

4. The bag catheter of claim 2, further comprising a conventional second drainage portal formed in said shaft and communicating with said drainage tube, said second drainage portal being situated between said first drainage portal and said distal end of said shaft.

5. The bag catheter of claim 2, wherein said first drainage portal is elongated a first length along said shaft; and wherein said at least one balloon is elongated a second length along said shaft, said second length being longer than said first length.

6. The bag catheter of claim 5, wherein said first drainage portal has a proximate portal end and said at least one balloon has a proximate balloon end, said proximate portal end being located a distance substantially between 1 and 2 millimeters from said proximate balloon end as measured in a direction toward said distal end of said shaft.

7. The bag catheter of claim 1, wherein said at least one balloon comprises a plurality of balloons.

8. The bag catheter of claim 7, wherein said channel means comprises:
    seal means for fluidically sealing said plurality of balloons with respect to said first drainage portal; and
    fluid channel means for selectively introducing the pressurized fluid to said plurality of balloons;
    wherein said fluid channel means and said drainage tube are respectively sealed so that said fluid channel means and said drainage tube are fluidically independent of each other.

9. The bag catheter of claim 1, wherein said at least one balloon comprises a single balloon.

10. The bag catheter of claim 9, wherein said channel means comprises:
    seal means for fluidically sealing said single balloon with respect to said first drainage portal; and
    fluid channel means for selectively introducing the pressurized fluid to said single balloon;
    wherein said fluid channel means and said drainage tube are respectively sealed so that said fluid channel means and said drainage tube are fluidically independent of each other.

11. A bag catheter comprising:
    an elongated flexible shaft having a proximate end and an opposite distal end, a distal end portion of said shaft including said distal end, said flexible shaft comprising:
        a first drainage portal formed in said shaft at said distal end portion thereof;
        a drainage tube formed in said shaft, said drainage tube fluidically communicating with said first drainage portal;
        balloon means for being selectively inflated by a pressurized fluid, said balloon means having a proximal end and a distal end, said balloon means being attached to said shaft between said proximal and distal ends of said balloon means, wherein said proximal and distal ends of said balloon means are located on either side of said first drainage portal such that said balloon means inflates outwardly in relation to said shaft and outwardly adjacent said first drainage portal without occluding said first drainage portal;

seal means for fluidically sealing said balloon means with respect to said first drainage portal; and fluid channel means fluidically communicating with said balloon means for selectively introducing the pressurized fluid to said balloon means;

wherein said fluid channel means and said drainage tube are respectively sealed so that said fluid channel means and said drainage tube are fluidically independent of each other.

12. The bag catheter of claim 11, wherein said fluid channel means comprises:

an inflation channel; and fluid entry means for providing a site of introduction of the pressurized fluid into said inflation channel.

13. The bag catheter of claim 12, wherein said first drainage portal is elongated a first length along said shaft; and wherein said balloon means is elongated a second length along said shaft, said second length being longer than said first length.

14. The bag catheter of claim 13, wherein said first drainage portal has a proximate portal end and said balloon means has a proximate balloon end, said proximate portal end being located a distance substantially between 1 and 2 millimeters from said proximate balloon end as measured in a direction toward said distal end of said shaft.

15. The bag catheter of claim 14, further comprising a conventional second drainage portal formed in said shaft and communicating with said drainage tube, said second drainage portal being situated between said first drainage portal and said distal end of said shaft.

16. A bag catheter comprising:

an elongated flexible shaft having a proximate end and an opposite distal end, a distal end portion of said shaft including said distal end, said flexible shaft comprising:

an inflation channel;

fluid entry means for providing a site of introduction of a pressurized fluid into said inflation channel;

a first drainage portal formed in said shaft at said distal end portion thereof;

a drainage tube formed in said shaft, said drainage tube fluidically communicating with said first drainage portal;

balloon means for being selectively inflated by pressurized fluid introduced into said inflation channel, said balloon means having a proximal end and a distal end, said balloon means being attached to said shaft between said proximal and distal ends of said balloon means, wherein said proximal and distal ends of said balloon means are located on either side of said first drainage portal such that said balloon means inflates outwardly in relation to said shaft and outwardly around said first drainage portal without occluding said first drainage portal; and seal means for fluidically sealing said balloon means with respect to said first drainage portal;

wherein said inflation channel and said drainage tube are respectively sealed so that said inflation channel and said drainage tube are fluidically independent of each other; and wherein said first drainage portal is elongated a first length along said shaft; and wherein said balloon means is elongated a second length along said shaft, said second length being longer than said first length.

17. The bag catheter of claim 16, wherein said first drainage portal has a proximate portal end and said balloon means has a proximate balloon end, said proximate portal end being located a distance substantially between 1 and 2 millimeters from said proximate balloon end as measured in a direction toward said distal end of said shaft.

18. The bag catheter of claim 17, further comprising a conventional second drainage portal formed in said shaft and communicating with said drainage tube, said second drainage portal being situated between said first drainage portal and said distal end of said shaft.

* * * * *